US012788692B2

(12) United States Patent
Drapeau et al.

(10) Patent No.: US 12,788,692 B2
(45) Date of Patent: Nov. 10, 2026

(54) COMPOSITIONS FOR IMPROVED SKIN APPEARANCE AND METHODS OF USE THEREOF

(71) Applicant: Biomx Stemceuticals, LLC, Austin, TX (US)

(72) Inventors: Christian Drapeau, Austin, TX (US); Shakahn Kukulcan, Austin, TX (US)

(73) Assignee: BIOMX STEMCEUTICALS, LLC, Austin, TX (US)

( * ) Notice: Subject to any disclaimer, the term of this patent is extended or adjusted under 35 U.S.C. 154(b) by 471 days.

(21) Appl. No.: 18/246,584

(22) PCT Filed: Sep. 24, 2021

(86) PCT No.: PCT/US2021/051897

§ 371 (c)(1),
(2) Date: Mar. 24, 2023

(87) PCT Pub. No.: WO2022/067002

PCT Pub. Date: Mar. 31, 2022

(65) Prior Publication Data

US 2023/0363988 A1 Nov. 16, 2023

Related U.S. Application Data

(60) Provisional application No. 63/082,895, filed on Sep. 24, 2020.

(51) Int. Cl.

| | |
|---|---|
| ***A61K 8/25*** | (2006.01) |
| ***A61K 8/19*** | (2006.01) |
| ***A61K 8/34*** | (2006.01) |
| ***A61K 8/365*** | (2006.01) |
| ***A61K 8/44*** | (2006.01) |
| ***A61K 8/60*** | (2006.01) |
| ***A61K 8/64*** | (2006.01) |
| ***A61K 8/67*** | (2006.01) |
| ***A61K 8/73*** | (2006.01) |
| ***A61K 8/9789*** | (2017.01) |
| ***A61K 8/9794*** | (2017.01) |
| ***A61K 8/98*** | (2006.01) |
| ***A61Q 19/08*** | (2006.01) |

(52) U.S. Cl.
CPC .................. *A61K 8/25* (2013.01); *A61K 8/19* (2013.01); *A61K 8/347* (2013.01); *A61K 8/365* (2013.01); *A61K 8/445* (2013.01); *A61K 8/60* (2013.01); *A61K 8/64* (2013.01); *A61K 8/671* (2013.01); *A61K 8/676* (2013.01); *A61K 8/735* (2013.01); *A61K 8/9789* (2017.08); *A61K 8/9794* (2017.08); *A61K 8/987* (2013.01); *A61Q 19/08* (2013.01); *A61K 2800/28* (2013.01); *A61K 2800/884* (2013.01)

(58) Field of Classification Search
CPC . A61K 8/25; A61K 8/19; A61K 8/365; A61K 8/445; A61K 8/64; A61K 8/671; A61K 8/676; A61K 2800/28; A61K 8/347; A61K 8/60; A61K 8/735; A61K 8/9789; A61K 8/9794; A61K 8/987; A61K 2800/884; A61K 2800/43; A61K 2800/436; A61K 8/73; A61K 8/97; A61Q 19/08; A61Q 19/00
See application file for complete search history.

(56) References Cited

U.S. PATENT DOCUMENTS

| | | | | |
|---|---|---|---|---|
| 2005/0214332 A1* | 9/2005 | Osborne | A61K 8/675 424/70.13 |
| 2010/0068232 A1 | 3/2010 | Key | |
| 2016/0008297 A1* | 1/2016 | Schmaus | A61Q 19/02 424/59 |
| 2017/0156999 A1* | 6/2017 | Harris | A45D 34/00 |
| 2019/0099340 A1* | 4/2019 | Fields | A61K 8/34 |
| 2020/0030349 A1 | 1/2020 | Schantl | |

FOREIGN PATENT DOCUMENTS

| | | | |
|---|---|---|---|
| CA | 3076107 A1 * | 3/2019 | A61Q 19/08 |
| CN | 104586710 | 5/2015 | |
| CN | 106492268 | 3/2017 | |
| CN | 106963720 A * | 7/2017 | A61K 8/988 |
| CN | 104644523 | 7/2018 | |
| CN | 109125204 | 1/2019 | |
| KR | 20170012735 | 2/2017 | |
| RU | 2654804 C2 * | 5/2018 | |
| WO | WO-2013020182 A1 * | 2/2013 | A61K 8/676 |

(Continued)

OTHER PUBLICATIONS

Machine translated English copy, Dreher (RU2654804, May 24, 2018), [Retrieved on May 7, 2025].*
ISM, Mesh and Micron Sizes, Industrial Specialties Mfg. and IS MED Specialties, Mar. 1, 2020 (Year: 2020).*
English machine translated CN106963720, Jul. 21, 2017, [Retrieved on Sep. 25, 2025] Retrieved from Espacenet <https://worldwide.espacenet.com/publication Details/> (Year: 2017).*
Adams & Scadden, The hematopoietic stem cell in its place. *Nature Immunology* 7:333-337 (2006).
Blanpain & Fuchs, Epidermal Stem Cells of the Skin. *Annu Rev Cell Dev Biol* 22:339-373 (2006).
Diegelmann & Evans, Wound healing: An overview of acute, fibrotic and delayed healing. *Front Biosci* 9:283-289 (2004).
Hall et al., The comparative role of activator protein 1 and Smad factors in the regulation of Timp-1 and MMP-1 gene expression by transforming growth factor-beta 1, *J Biol Chem* 278:10304-10313 (2003).

(Continued)

*Primary Examiner* — Sue X Liu
*Assistant Examiner* — Dongxiu Zhang
(74) *Attorney, Agent, or Firm* — pH IP Law

(57) ABSTRACT

The present disclosure is directed to methods and compositions for improving skin appearance and health. In some aspects, a method of conditioning the skin is provided comprising applying a microdermabrasion composition to the skin, applying a regenerative cosmeceutical composition to the skin, and treating with a nutricosmetic composition. The present disclosure also provides kits comprising compositions for improving skin appearance and health.

13 Claims, 4 Drawing Sheets

(56) References Cited

FOREIGN PATENT DOCUMENTS

WO WO 2022/067002 3/2022

OTHER PUBLICATIONS

Herouy, Matrix metalloproteinases in skin pathology (review). *Int J Mol Med* 7:3-12 (2001).
Hong et al., Immunohistological localization of endogenous unlabeled stem cells in wounded skin. *J Histochem Cytochem* 62:276-285 (2014).
Hunt, The physiology of wound healing. *Ann Emergency Med* 17:1265-1273 (1988).
Jimi et al. G-CSF Administration Accelerates Cutaneous Wound Healing Accompanied With Increased Pro-Hyp Production In db/db Mice. Clin Res Dermatol Open Access 4(1): 1-9.
Lin Q, et al. Pharmacological mobilization of endogenous stem cells significantly promotes skin regeneration after full-thickness excision: the synergistic activity of AMD3100 and tacrolimus. J Invest Dermatol. Sep. 2014;134(9):2458-2468.
Matrisian, The matrix-degrading metalloproteinases. *Bioessays* 14:455-463 (1992).
Maxson et al., Concise Review: Role of Mesenchymal Stem Cells in Wound Repair. *Stem Cells Translational Medicine* 1:142-149 (2012).
Paladini et al., Onset of re-epithelialization after skin injury correlates with a reorganization of keratin filaments in wound edge keratinocytes: defining a potential role for keratin 16. *J Cell Biol* 132:381-397 (1996).
Parks, Matrix metalloproteinases in repair. *Wound Repair Regen* 7:423-432 (1999).
PCT International Search Report and Written Opinion issued in International Application No. PCT/US2021051897, mailed Feb. 2, 2022.
Sasaki M, et al. Mesenchymal stem cells are recruited into wounded skin and contribute to wound repair by transdifferentiation into multiple skin cell type. J Immunol. Feb. 15, 2008;180(4):2581-7.
Tonnesen et al., Angiogenesis in wound healing. *J Invest Dermatol Symp Proc* 5:40-46 (2000).
Velnar et al., The wound healing process: An overview of the cellular and molecular mechanisms. *J Int Med Res* 37:1528-1542 (2009).
Wang & Chang, Induction of Disease-Associated Keratin 16 Gene Expression by Epidermal Growth Factor Is Regulated through Cooperation of Transcription Factors Sp1 and c-Jun. *J Biol Chem* 278:45848-45857 (2003).
Wang et al., Activation of extracellular signal-regulated kinase signaling by epidermal growth factor mediates c-Jun activation and p300 recruitment in keratin 16 gene expression. *Molecular Pharmacology* 69:85-98 (2006).

* cited by examiner

COMPOSITIONS FOR IMPROVED SKIN APPEARANCE AND METHODS OF USE THEREOF

PRIORITY CLAIM

This application is a national phase application under 35 U.S.C. § 371 of International Application No. PCT/US2021/051897, filed Sep. 24, 2021, which claims benefit of priority to U.S. Provisional Application Ser. No. 63/082,895, filed Sep. 24, 2020, the entire contents of each of which is hereby incorporated by reference.

BACKGROUND

1. Field

The present application relates generally to the field of cosmetology, skin care, cosmeceuticals and nutricosmetics. More particularly, it concerns methods for conditioning the skin comprising compositions and kits comprising the same.

2. Description of Related Art

Described herein are methods combining the use of microdermabrasion with the topical application of botanical extracts and other cosmeceuticals, along with the consumption of nutricosmetic ingredients, to provide beneficial effects for improved collagen production, fibroblast proliferation, antioxidant protection, free radical inhibition, and ultimately overall skin repair and renewal. Combinations of these three different approaches exhibit synergistic effects, leading to dramatic improvements in skin moisture levels, wrinkle reduction, elasticity and overall skin appearance.

SUMMARY

In some aspects, the present disclosure provides methods of conditioning the skin of a subject in need thereof, comprising:

a) applying a microdermabrasion composition to a skin surface of a subject; and c) applying a regenerative composition to the skin surface of the subject, wherein said subject has been treated with a nutricosmetic composition.

In further aspects, the present disclosure provides methods of conditioning the skin of a subject in need thereof, comprising:

a) applying a microdermabrasion composition to a skin surface of a subject;

b) applying a transdermal penetrant allowing macromolecule to penetrate the stratum corneum; and c) applying a regenerative composition to the skin surface of the subject, wherein said subject has been treated with a nutricosmetic composition.

In some embodiments, the methods further comprise administering the nutricosmetic composition to the subject. In some embodiments, the microdermabrasion composition comprises one or more abrasive agents, the abrasive agents are solid particles selected from the group consisting of: pearl, diamond, hematite, silicon dioxide, aluminum oxide, or bamboo particles. In some embodiments, the total concentration of the one or more abrasive agents in the microdermabrasion composition is from about 3% to about 50% w/w. In further embodiments, the total concentration of the one or more abrasive agents in the microdermabrasion composition is from about 10% to about 40% w/w. In some embodiments, the total concentration of the one or more abrasive agents in the microdermabrasion composition is about 10% w/w. In other embodiments, the total concentration of the one or more abrasive agents in the microdermabrasion composition is about 20% w/w. In still other embodiments, the total concentration of the one or more abrasive agents in the microdermabrasion composition is about 30% w/w. In yet other embodiments, the total concentration of the one or more abrasive agents in the microdermabrasion composition is about 40% w/w. In some embodiments, the total concentration of the one or more abrasive agents in the microdermabrasion composition is about 22% w/w. For example, in some aspects, the total concentration of the one or more abrasive agents in the microdermabrasion composition is about 10% to 40%; 15% to 30%; or 20% to 25%.

In some embodiments, the microdermabrasion composition comprises pearl particles. In some embodiments, the microdermabrasion composition comprises diamond particles. In some embodiments, the microdermabrasion composition comprises silicon dioxide particles. In some embodiments, the microdermabrasion composition comprises bamboo particles. In some embodiments, the microdermabrasion composition comprises pearl, silicon dioxide, and bamboo particles. In some embodiments, the total concentration of the pearl particles in the microdermabrasion composition is from about 2% to about 15% w/w. In further embodiments, the total concentration of the pearl particles in the microdermabrasion composition is from about 8% to about 10% w/w. In some embodiments, the total concentration of the silicon dioxide particles in the microdermabrasion composition is from about 2% to about 15% w/w. In further embodiments, the total concentration of the silicon dioxide particles in the microdermabrasion composition is from about 8% to about 10% w/w. In some embodiments, the total concentration of the bamboo particles in the microdermabrasion composition is from about 2% to about 15% w/w. In further embodiments, the total concentration of the bamboo particles in the microdermabrasion composition is from about 8% to about 10% w/w.

In some embodiment the transdermal penetrant composition comprises one or more compounds selected from the group consisting of: alkanes, laurocapram, oil of *Citrus sinensis*, oleic acid and squalene. In some embodiments the alkanes are extracted from coconut oil or derived from petroleum sources. In some embodiments the squalene is extracted from olive oil, amaranth, rice bran, wheat germ or shark liver.

In some embodiments, the concentration of each of the one or more penetrating agents is independently from about 0.1% to about 5%. In some embodiments, the concentration of each of the one or more penetrating agents is independently from about 0.5% to about 5%. In some embodiments, the concentration of each of the one or more penetrating agents is independently from about 1% to about 5%. In some embodiments, the concentration of each of the one or more penetrating agents is independently from about 1% to about 3%.

In some embodiments, the regenerative composition comprises one or more regenerative agents selected from the group consisting of: a stem cell-derived cytokine, retinol or a retinol derivative, phenylalanine or a phenylalanine derivative, glucosamine or a glucosamine derivative, methylglucoside-6-phosphate (MG6P) proline lysine copper complex, ferulic acid or a ferulic acid derivative, *Physalis angulata* or an extract thereof, ascorbic acid or an ascorbic acid derivative, and hyaluronic acid or a hyaluronic acid derivative. In some embodiments, the regenerative composition comprises a stem cell-derived cytokine. In some embodiments, the stem-cell derived cytokine is Human Prolactin or a bio-equivalent, Human Placental Lactogen or a bio-equivalent, Human Epidermal Growth Factor or a bio-equivalent (EGF), Human Fibroblast Growth Factor-1 of a bio-equivalent (FGF-1), Human Stem Cell Factor or a bio-equivalent (SCF), Human Thymosin beta-4 or a bio-equivalent, Human Fibroblast Growth Factor-2 or a bio-equivalent (FGF-2), Human Vasoactive Intestinal Peptide or a bio-equivalent (VIP). In some embodiments, the regenerative composition comprises retinol or a retinol derivative. In some embodiments, the retinol derivative is retinoic acid, hydroxypinacolone retinoate, or retinyl retinoate. In some embodiments, the retinol derivative is hydroxypinacolone retinoate. In some embodiments, the regenerative composition comprises phenylalanine or a phenylalanine derivative. In some embodiments, the phenylalanine derivative is undecylenoyl phenylalanine. In some embodiments, the regenerative composition comprises glucosamine or a glucosamine derivative. In some embodiments, the glucosamine derivative is acetyl glucosamine phosphate, N-acetyl glucosamine-6-phosphate, or N-acetyl-D-glucosamine. In some embodiments, the glucosamine derivative is N-acetyl-D-glucosamine. In some embodiments, the regenerative composition comprises a MG6P proline lysine copper complex. In some embodiments, the regenerative composition comprises ferulic acid or a ferulic acid derivative. In some embodiments, the regenerative composition comprises *physalis angulata* or an extract thereof. In some embodiments, the regenerative composition comprises ascorbic acid or an ascorbic acid derivative. In some embodiments, the ascorbic acid derivative is aminopropyl ascorbyl phosphate, ascorbyl-6-palmitate, 3-O-ethyl ascorbic acid, ascorbyl glucoside or magnesium ascorbyl phosphate. In some embodiments, the regenerative composition comprises hyaluronic acid or a hyaluronic acid derivative. In some embodiments, the hyaluronic acid derivative is hyaluronan, low molecular weight hydrolyzed sodium hyaluronate, high molecular weight hydrolyzed sodium hyaluronate, or fermented hyaluronic acid.

In some embodiments, the concentration of each of the one or more regenerative agents is independently from about 0.05% to about 5%. In some embodiments, the concentration of each of the one or more regenerative agents is independently from about 0.1% to about 5%. In some embodiments, the concentration of each of the one or more regenerative agents is independently from about 0.1% to about 1%. In some embodiments, the concentration of each of the one or more regenerative agents is independently from about 0.5% to about 2%. In some embodiments, the concentration of each of the one or more regenerative agents is independently from about 1% to about 3%.

In some embodiments, the nutricosmetic composition comprises one or more nutricosmetic agents selected from the group consisting of: a ceramide, helicogenic amino acids, hyaluronic acid or a hyaluronic acid derivative, glucosamine or a glucosamine derivative, and resveratrol. In some embodiments, the nutricosmetic composition comprises a helicogenic amino acid, such as glycine, hydroxyproline, proline, or alanine. In some embodiments, the nutricosmetic composition comprises hyaluronic acid or a hyaluronic acid derivative. In some embodiments, the hyaluronic acid derivative is hyaluronan, low molecular weight hydrolyzed sodium hyaluronate, ultra-low molecular weight hydrolyzed sodium hyaluronate, or fermented hyaluronic acid. In some embodiments, the nutricosmetic composition comprises glucosamine or a glucosamine derivative, such as N-acetyl-D-glucosamine.

In some embodiments, the nutricosmetic composition comprises resveratrol. In some embodiments, the resveratrol is isolated from *Vitis vinifera* (red grape), *Polygonum cuspidatum* (Japanese knotweed), and/or *Vaccinium corymbosum* (blueberry). In some embodiments, the nutricosmetic composition is formulated as a unit dose. In some embodiments, the nutricosmetic composition is administered once. In other embodiments, the nutricosmetic composition is administered more than once. In some embodiments, the nutricosmetic composition is administered daily. In some embodiments, the total daily dose administered of each of the one or more nutricosmetic agents is independently from about 0.01 g to 5 g. In some embodiments, the total daily dose administered of each of the one or more nutricosmetic agents is independently from about 0.05 g to 5 g; 0.1 g to 5 g or 1 g to 5 g. In some embodiments, the total daily dose administered of each of the one or more nutricosmetic agents is independently from about 0.05 g to 3 g; 0.1 g to 3 g or 1 g to 3 g. In some embodiments, the total daily dose administered of each of the one or more nutricosmetic agents is independently from about 0.1 g to 2 g. In some embodiments, wherein the total daily dose administered of each of the one or more nutricosmetic agents is independently from about 0.1 g to 1.5 g. In some embodiments, wherein the total daily dose administered of each of the one or more nutricosmetic agents is independently from about 0.1 g to 1 g. In some embodiments, wherein the total daily dose administered of each of the one or more nutricosmetic agents is independently from about 0.25 g to 2.5 g. In some embodiments, wherein the total daily dose administered of each of the one or more nutricosmetic agents is independently from about 0.25 g to 1 g. In some embodiments, wherein the total daily dose administered of each of the one or more nutricosmetic agents is independently from about 0.1 g to 2 g. In some embodiments, wherein the total daily dose administered of each of the one or more nutricosmetic agents is independently from about 0.1 g to 0.5 g. In some embodiments, the total daily dose administered of each of the one or more nutricosmetic agents is independently from about 0.1 g to 0.2 g. In some embodiments, the total daily dose administered of each of the one or more nutricosmetic agents is independently from about 0.01 g to 0.5 g. In some embodiments, the total daily dose administered of each of the one or more nutricosmetic agents is independently from about 0.01 g to 0.1 g.

In some embodiments, the nutricosmetic composition is formulated as a powder, a liquid, or a gel. In some embodiments, the nutricosmetic composition is administered orally. In some embodiments, the subject is a human. In some embodiments, the method enhances the appearance of the skin. In some embodiments, the method enhances skin tone. In some embodiments, the method enhances skin moisture or hydration. In some embodiments, the method enhances the skin elasticity. In some embodiments, the method reduces fine lines and/or wrinkles. In some embodiments, the method enhances collagen formation.

In some embodiments, method (e.g., a penetrant method) comprises:

a) applying a microdermabrasion composition to a skin surface of a subject, wherein the microdermabrasion composition comprises pearl particles; and c) applying a regenerative composition to the skin surface of the subject, wherein the regenerative composition comprises hydroxypinacolone retinoate, undecylenoyl phenylalanine, N-acetyl-D-glucosamine, MG6P proline lysine copper complex, *Physalis angulata* or an extract thereof, ferulic acid, aminopropyl ascorbyl phosphate, 3-O-ethyl ascorbic acid, and low molecular weight hydrolyzed sodium hyaluronate, further wherein said subject has been treated with a nutricosmetic composition, wherein the nutricosmetic composition comprises glycine, hydroxyproline, proline, alanine, ascorbic acid derivatives, hyaluronic acid, N-acetyl-D-glucosamine, ceramides and resveratrol.

In some embodiments, method (e.g., a penetrant method) comprises:

a) applying a microdermabrasion composition to a skin surface of a subject, wherein the microdermabrasion composition comprises pearl particles;
b) applying a transdermal penetrant allowing macromolecule to penetrate the stratum corneum, wherein the transdermal penetrant composition comprises coconut alkanes, laurocapram, *Citrus sinensis* oil, oleic acid and sualene; and
c) applying a regenerative composition to the skin surface of the subject, wherein the regenerative composition comprises hydroxypinacolone retinoate, undecylenoyl phenylalanine, N-acetyl-D-glucosamine, MG6P proline lysine copper complex, *Physalis angulata* or an extract thereof, ferulic acid, aminopropyl ascorbyl phosphate, 3-O-ethyl ascorbic acid, and low molecular weight hydrolyzed sodium hyaluronate, further wherein said subject has been treated with a nutricosmetic composition, wherein the nutricosmetic composition comprises glycine, hydroxyproline, proline, alanine, ascorbic acid derivatives, hyaluronic acid, N-acetyl-D-glucosamine, ceramides and resveratrol.

In another aspect, the present disclosure provides kits comprising: a) a topical microdermabrasion composition; b) a topical transdermal penetrant, c) a topical regenerative cosmeceutical composition; and d) a nutricosmetic composition. In some embodiments, the microdermabrasion composition comprises one or more abrasive agents, wherein the abrasive agents are solid particles selected from the group consisting of: pearl, diamond, hematite, silicon dioxide, aluminum oxide, or bamboo particles. In some embodiments, the total concentration of the one or more abrasive agents in the microdermabrasion composition is from about 5% to about 50% w/w. In further embodiments, the total concentration of the one or more abrasive agents in the microdermabrasion composition is from about 10% to about 40% w/w. In some embodiments, the total concentration of the one or more abrasive agents in the microdermabrasion composition is about 10% w/w. In other embodiments, the total concentration of the one or more abrasive agents in the microdermabrasion composition is about 20% w/w. In still other embodiments, the total concentration of the one or more abrasive agents in the microdermabrasion composition is about 30% w/w. In yet other embodiments, the total concentration of the one or more abrasive agents in the microdermabrasion composition is about 40% w/w.

In some embodiments, the microdermabrasion composition comprises pearl particles. In some embodiments, the microdermabrasion composition comprises diamond particles. In some embodiments, the microdermabrasion composition comprises silicon dioxide particles. In some embodiments, the microdermabrasion composition comprises bamboo particles. In some embodiments, the microdermabrasion composition comprises pearl, silicon dioxide, and bamboo particles. In some embodiments, the total concentration of the pearl particles in the microdermabrasion composition is from about 2% to about 15% w/w. In further embodiments, the total concentration of the pearl particles in the microdermabrasion composition is from about 8% to about 10% w/w. In some embodiments, the total concentration of the silicon dioxide particles in the microdermabrasion composition is from about 2% to about 15% w/w. In further embodiments, the total concentration of the silicon dioxide particles in the microdermabrasion composition is from about 3% to about 8% w/w. In some embodiments, the total concentration of the bamboo particles in the microdermabrasion composition is from about 2% to about 15% w/w. In further embodiments, the total concentration of the bamboo particles in the microdermabrasion composition is from about 2% to about 8% w/w. In some embodiments, the microdermabrasion composition is formulated for topical administration.

In some embodiment the transdermal penetrant composition comprises one or more compounds selected from the group consisting of: alkanes, laurocapram, oil of *Citrus sinensis*, oleic acid and squalene. In some embodiments the alkanes are extracted from coconut oil or derived from petroleum sources. In some embodiments the squalene is extracted from olive oil, amaranth, rice bran, wheat germ or shark liver.

In some embodiments, the total concentration of the one or more penetrating agents is from about 1% to about 25% w/w. In further embodiments, the total concentration of the one or more penetrating agents is from about 2% to about 20% w/w. In some embodiments, the total concentration of the one or more penetrating agents is from about 3% to about 15% w/w. In some embodiments, the concentration of the one or more penetrating agents is from about 1% to about 12% w/w. In yet other embodiments, the total concentration of the one or more penetrating agents is about 10% to about 15% w/w.

In some embodiments, the regenerative composition comprises one or more regenerative agents selected from the group consisting of: a stem cell-derived cytokine, retinol or a retinol derivative, phenylalanine or a phenylalanine derivative, glucosamine or a glucosamine derivative, methylglucoside-6-phosphate (MG6P) proline lysine copper complex, ferulic acid or a ferulic acid derivative, *physalis angulata* or an extract thereof, ascorbic acid or an ascorbic acid derivative, and hyaluronic acid or a hyaluronic acid derivative. In some embodiments, the regenerative composition comprises a stem cell-derived cytokine. In some embodiments, the stem-cell derived cytokine is Human Prolactin or a bio-equivalent, Human Placental Lactogen or a bio-equivalent, Human Epidermal Growth Factor or a bio-equivalent (EGF), Human Fibroblast Growth Factor-1 of a bio-equivalent (FGF-1), Human Stem Cell Factor or a bio-equivalent (SCF), Human Thymosin beta-4 or a bio-equivalent, Human Fibroblast Growth Factor-2 or a bio-equivalent (FGF-2), Human Vasoactive Intestinal Peptide or a bio-equivalent (VIP). In some embodiments, the regenerative composition comprises retinol or a retinol derivative. In some embodiments, the retinol derivative is hydroxypinacolone retinoate or retinyl retinoate. In some embodiments, the retinol derivative is hydroxypinacolone retinoate. In some embodiments, the regenerative composition comprises phenylalanine or a phenylalanine derivative. In some embodiments, the phenylalanine derivative is undecylenoyl phenylalanine. In some embodiments, the regenerative composition comprises glucosamine or a glucosamine derivative, such as acetyl glucosamine phosphate, N-acetyl glucosamine-6-phosphate, or N-acetyl-D-glucosamine. In some embodiments, the regenerative composition comprises a MG6P proline lysine copper complex. In some embodiments, the regenerative composition comprises ferulic acid or a ferulic acid derivative. In some embodiments, the regenerative composition comprises *physalis angulata* or an extract thereof. In some embodiments, the regenerative composition comprises ascorbic acid or an ascorbic acid derivative. In some embodiments, the ascorbic acid derivative is aminopropyl ascorbyl phosphate, ascorbyl-6-palmitate, 3-O-ethyl ascorbic acid, ascorbyl glucoside or magnesium ascorbyl phosphate. In some embodiments, the regenerative composition comprises hyaluronic acid or a hyaluronic acid derivative. In some embodiments, the hyaluronic acid derivative is hyaluronan, low molecular weight hydrolyzed sodium hyaluronate, ultra-low molecular weight hydrolyzed sodium hyaluronate, or fermented hyaluronic acid.

In some embodiments, the concentration of each of the one or more regenerative agents is independently from about 0.05% to about 5%, 0.1% to 4%, or 0.5% to 3%. In a preferred aspect, the concentration of each of the one or more regenerative agents is independently from about 0.3% to 2%. In some embodiments, the concentration of each of the one or more regenerative agents is independently from about 0.1% to about 5%. In some embodiments, the concentration of each of the one or more regenerative agents is independently from about 0.1% to about 1%. In some embodiments, the concentration of each of the one or more regenerative agents is independently from about 0.5% to about 2%. In some embodiments, the concentration of each of the one or more regenerative agents is independently from about 1% to about 3%. In some embodiments, the regenerative composition is formulated for topical administration.

In some embodiments, the total amount of regenerative agents is from about 5% to 25%. In a preferred aspect, the regenerative agents is from about 10% to 20%, or 12% to 18%. In some embodiments, the total concentration of the regenerative agents about 15%.

In some embodiments, the nutricosmetic composition comprises one or more nutricosmetic agents selected from the group consisting of: a ceramide, a helicogenic amino acid, hyaluronic acid or a hyaluronic acid derivative, glucosamine or a glucosamine derivative, and resveratrol. In some embodiments, the nutricosmetic composition comprises a helicogenic amino acid, such as glycine, hydroxyproline, proline, or alanine. In some embodiments, the nutricosmetic composition comprises hyaluronic acid or a hyaluronic acid derivative. In some embodiments, the hyaluronic acid derivative is hyaluronan, hydrolyzed sodium hyaluronate, or fermented hyaluronic acid. In some embodiments, the nutricosmetic composition comprises glucosamine or a glucosamine derivative. In some embodiments, the glucosamine derivative is N-acetyl-D-glucosamine. In some embodiments, the nutricosmetic composition comprises resveratrol. In some embodiments, the resveratrol is isolated from *Vitis vinifera* (red grape), *Fallopia japonica* or *Polygonum cuspidatum* (Japanese knotweed), and/or *Vaccinium corymbosum* (blueberry).

In some embodiments, the regenerative composition is formulated for topical administration. In some embodiments, the transdermal penetrant composition is formulated for topical administration. In some embodiments, the nutricosmetic composition is formulated as a unit dose. In some embodiments, the nutricosmetic composition is administered once. In other embodiments, the nutricosmetic composition is administered more than once. In some embodiments, the nutricosmetic composition is administered daily. In some embodiments, the nutricosmetic composition is formulated such that each of the one or more nutricosmetic agents is independently from about 0.01 g to 5 g. In some embodiments, the nutricosmetic composition is formulated such that each of the one or more nutricosmetic agents is independently from about 1 g to 5 g. In some embodiments, the nutricosmetic composition is formulated such that each of the one or more nutricosmetic agents is independently from about 1 g to 3 g. In some embodiments, the nutricosmetic composition is formulated such that each of the one or more nutricosmetic agents is independently from about 0.5 g to 5 g. In some embodiments, the nutricosmetic composition is formulated such that each of the one or more nutricosmetic agents is independently from about 0.5 g to 1.5 g. In some embodiments, the nutricosmetic composition is formulated such that each of the one or more nutricosmetic agents is independently from about 0.3 g to 1 g. In some embodiments, the nutricosmetic composition is formulated such that each of the one or more nutricosmetic agents is independently from about 0.25 g to 2.5 g. In some embodiments, the nutricosmetic composition is formulated such that each of the one or more nutricosmetic agents is independently from about 0.25 g to 1 g. In some embodiments, the nutricosmetic composition is formulated such that each of the one or more nutricosmetic agents is independently from about 0.1 g to 2 g. In some embodiments, the nutricosmetic composition is formulated such that each of the one or more nutricosmetic agents is independently from about 0.1 g to 0.5 g. In some embodiments, the nutricosmetic composition is formulated such that each of the one or more nutricosmetic agents is independently from about 0.1 g to 0.2 g. In some embodiments, the nutricosmetic composition is formulated such that each of the one or more nutricosmetic agents is independently from about 0.01 g to 0.5 g. In some embodiments, the nutricosmetic composition is formulated such that each of the one or more nutricosmetic agents is independently from about 0.01 g to 0.1 g.

In some embodiments, the nutricosmetic composition is formulated as a powder, a liquid, or a gel. In some embodiments, the nutricosmetic composition is formulated for oral administration.

In some embodiments, the kit comprises:

a) a microdermabrasion composition, wherein the microdermabrasion composition comprises pearl particles; and b) a transdermal penetrant composition, wherein the penetrating composition comprises alkanes, laurocapram, oil of *Citrus sinensis*, oleic acid and squalene.

c) a regenerative composition, wherein the regenerative composition comprises hydroxypinacolone retinoate, undecylenoyl phenylalanine, N-acetyl-D-glucosamine, MG6P proline lysine copper complex, *Physalis angulata* or an extract thereof, ferulic acid, aminopropyl ascorbyl phosphate, 3-O-ethyl ascorbic acid, ascorbyl glucoside and low molecular weight hydrolyzed sodium hyaluronate.

In some embodiments, the kit further comprises a nutricosmetic composition, wherein the nutricosmetic composition comprises glycine, hydroxyproline, proline, alanine, hyaluronic acid, N-acetyl-D-glucosamine, and resveratrol.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is preferably below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A shows semiquantitative analysis of Masson trichome-stainable collagen in the upper dermis after pearl nacre microdermabrasion.

FIG. 1B shows quantification of procollagen by Western analysis at 3 and 12 weeks after pearl nacre microdermabrasion. FIG. 1C shows semiquantitative analysis of papillary and reticular dermal fibroblast procollagen I mRNA by in situ hybridization at 3 and 12 weeks after microdermabrasion.

DESCRIPTION OF ILLUSTRATIVE EMBODIMENTS

I. The Present Embodiments

Figures 1A, 1B, 1C:
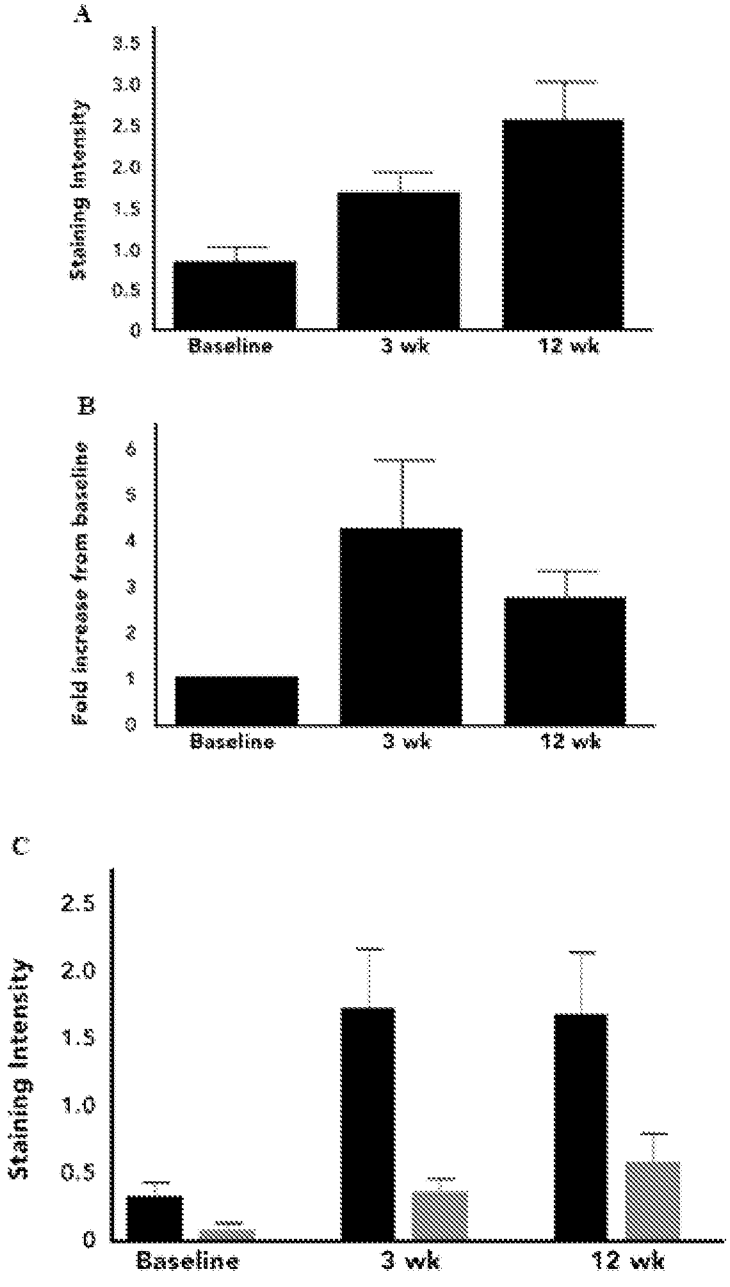
FIGS. 1A-1C show the impact of microdermabrasion (MDA) on various skin parameters, using a blend of pearl, silicon dioxide and bamboo particles at a concentration of 25%, with usage 3 times a week for 1 week.

In some aspects, the present disclosure provides methods combining the use of microdermabrasion with the topical application of herbal extracts and other cosmeceuticals, along with the consumption of nutricosmetic ingredients, to provide beneficial effects for improved collagen production, fibroblast proliferation, antioxidant protection, free radical inhibition, and ultimately overall skin repair and renewal. Combinations of these three different approaches exhibit synergistic effects, leading to dramatic improvements in skin moisture levels, wrinkle reduction, elasticity and overall skin appearance. In another aspect, the present disclosure provides kits comprising microdermabrasion compositions, topical regenerative compositions, and oral nutricosmetic compositions.

A. Background

The present disclosure is aimed at leveraging the natural process of tissue repair and renewal in the skin, by triggering a mild physiological injury and supporting various aspects of the natural process of tissue repair. To understand this invention, it is important to understand the normal process of skin repair before describing how this invention can lead to a reduction in wrinkles, fine lines, skin discoloration, skin hyperpigmentation, and even scar removal.

B. Skin Structure

The skin is composed of 3 layers called the epidermis, the dermis, and the hypodermis. The epidermis is the initial barrier of the body to the outside world. It is composed of a continuum of 5 layers that extends from the stratum basale where cells are regenerated every 12-14 days to the stratum corneum where keratinocytes are sloughed off as dead skin cells.

Below the stratum basale is the dermis composed of 2 layers, the papillary and reticular dermis. The papillary dermis contains the fibroblasts that produce a meshwork of type III collagen that anchors the epidermis to the dermis. The reticular dermis consists of type I collagen, elastin, and glycosaminoglycans, more importantly hyaluronic acid that can retain up to 1,000 its weight in water, making hyaluronic acid the main component to gain and retain skin moisture. In addition to connective tissue, the reticular dermis also contains nerve fibers, blood vessels, and sweat/sebaceous glands. The deepest layer is the hypodermis which is composed of loose connective tissue, fat and elastin important for anchoring the skin down to the bone and muscle.

Skin stem cells are found in various layers, both as part of the normal process of skin renewal and during wound repair. While epidermal stem cells mainly reside in the deepest layer of the epidermis, the stratum basale, in a region commonly referred to as the interfollicular epidermis, during an injury they are scattered in all layers of the skin, suggesting that they are supplied to the skin through capillaries localized in reticular dermis. [Hong et al., 2014]

C. Wound Healing Process

Normal wound healing is a dynamic and complex process involving a series of coordinated events, including bleeding and coagulation, acute inflammation, cell migration, proliferation, differentiation, angiogenesis, re-epithelialization, and synthesis and remodeling of extra cellular matrix (ECM). These complex events occur in four overlapping phases: (a) hemostasis, (b) inflammatory, (c) proliferative and (d) remodeling.

1. Hemostasis

In wound healing, the platelets are the cells that act as the initiators of the healing process. Aside from their role in the formation of a stable clot that stops the blood loss and seals the wound, platelets play a key role in skin repair by secreting growth factors such as platelet-derived growth factor, which is one of the key factors in initiating the subsequent healing steps. These growth factors recruit neutrophils and monocytes, stimulate epithelial cells and recruit fibroblasts.

2. Inflammatory Phase

While hemostasis is achieved, the inflammation phase begins. Neutrophils are the predominant cell type present 24-36 hours after injury. Guided by chemokines and other chemotactic agents, neutrophils move from the circulating blood into the wound environment where they remove foreign material, bacteria, dead cells, and damaged ECM by phagocytosis [21:22]. Mast cells are also active and they release granules filled with enzymes, histamine, and other active amines. These mediators are responsible for the characteristic signs of inflammation around the wound site: redness, heat, swelling, and pain. Monocytes, the precursors to macrophages, appear in the wound 48-72 hours after injury and continue the process of phagocytosis and tissue cleansing. Macrophages also act as key regulatory cells and produce numerous potent tissue growth factors, including transforming growth factor-β (TGF-β), tumor necrosis factor-α (TNF-α), epidermal growth factor (EGF), and fibroblast growth factor (FGF) [Maxson et al., 2012; Diegelmann and Evans, 2004]. These factors are integral in activating keratinocytes, fibroblasts, and endothelial cells into the next phase of tissue repair.

The initial phase of an injury is characterized by a series of reactions that include: A) expression of JunB and cJun proteins that are involved in the regulation of epidermal wound response and epidermal differentiation, including the production of matrix metalloproteinases (MMPs), cytokeratin-16, and inflammatory mediators, [Wang and Chang, 2003; Wang et al., 2006] B) induction of cytokeratin-16 by interfollicular keratinocytes, [Paladini et al., 1996] C) expression of matrix metalloproteinases (MMPs) that break down structural proteins that comprise the dermal extracellular matrix (ECM) and are critical for dermal remodeling during wound healing, [Herouy, 2001; Parks, 1999; Matrisian, 1992] and D) expression of interleukin-8 which is a powerful lymphocyte attractant.

3. Proliferative Phase

The proliferative phase typically starts on the fourth day after the initial injury and lasts for about 2 weeks. This phase is characterized by angiogenesis, collagen deposition, new tissue formation and epithelialization. Local factors in the wound microenvironment (low pH, reduced oxygen tension, and increased lactate) as well as growth factors (vascular endothelial cell growth factor [VEGF], fibroblast growth factor [FGF]) initiate and stimulate angiogenesis. [Tonnesen et al., 2000] In this process the pericytes regenerate the outer layers of capillaries and the endothelial cells produce the luminal lining. Endothelial stem cells recruited from the peripheral circulation also participates to angiogenesis. The TGF-β released earlier by platelets and macrophages is a critical signal, as it stimulates the fibroblasts to secrete the collagen framework (collagen, proteoglycans, and fibronectin) on which dermal regeneration takes place. [Hunt, 1988] At the same time, TGF-β decreases the secretion of proteases responsible for the breakdown of the matrix and stimulates the production of tissue inhibitor of metalloproteinases (TIMP). [Hall et al., 2003;]

In a healing wound, numerous growth factors secreted by immune cells also attract and activate stem cells originating from various locations including epidermal stem cells from the stratum basale and progenitor stem cells from the interfollicular epidermis (IFE). IFE progenitor stem cells also play a role in tissue renewal in the absence of injury. Recently, it was also reported that cytokines released in the wound can stimulate stem cells from the bulge of hair follicles, which are normally more quiescent, to exit their stem cell niche, proliferate, and differentiate to form the various cell types of the newly developing skin. [Blanpain and Fuchs, 2006; Hong et al., 2014]

During the healing process, there is a delicate balance between the MMPs and tissue inhibitors of metalloproteinases (TIMPs) so that there is a net production of new tissue. For example, in chronic wounds in which cell division and migration are suppressed, there are high levels of inflammatory cytokines and MMPs, and low levels of TIMPs and growth factors. [Diegelmann and Evans, 2004]

4. Remodeling Phase

Remodeling is the final phase of wound healing, which could last 6-12 months or even longer. This process involves remodeling and realignment of the collagen tissue to produce greater tensile strength, as well as a gradual shrinking that brings the wound margins closer together and reduces the size of the scar tissue. There is a gradual increase in TIMPs activity accompanied by a decrease in MMPs activity, leading to a stabilization of the new tissue. Finally, as the wound heals, the density of fibroblasts and macrophages is reduced by apoptosis. With time, the growth of capillaries stops, blood flow to the area declines, and metabolic activity decreases, resulting in a fully healed wound [Velnar et al., 2009].

D. Leverage and Support for the Natural Process of Skin Regeneration

In the context of the present disclosure, one method to leverage and support the natural process of skin repair and regeneration, for the purpose of reducing wrinkles, fine lines and increase overall facial radiance, is to create a mild physiological injury to the epidermis, which triggers a natural response of tissue repair and renewal. This step is followed by a support of the repair process by providing topically a series of components documented to support various aspects of skin repair, including but not limited to the stem cell migration and proliferation, fibroblast proliferation, collagen formation, expression of specific mRNA, angiogenesis, anti-inflammation and inhibition of MMPs. This is also accompanied by the oral intake of nutricosmetics such as collagen-derived amino acids, hyaluronate derivatives and vitamin C that constitute key ingredients for the optimal repair and renewal of the skin.

II. Definitions

"Administering" and/or "administer" as used herein refer to any route for delivering a pharmaceutical composition to a patient. Routes of delivery may include non-invasive peroral (through the mouth), topical (skin), transmucosal (nasal, buccal/sublingual, vaginal, ocular and rectal) and inhalation routes, as well as parenteral routes, and other methods known in the art. Parenteral refers to a route of delivery that is generally associated with injection, including intraorbital, infusion, intraarterial, intracarotid, intracapsular, intracardiac, intradermal, intramuscular, intraperitoneal, intrapulmonary, intraspinal, intrasternal, intrathecal, intrauterine, intravenous, sub arachnoid, subcapsular, subcutaneous, transmucosal, or transtracheal. Via the parenteral route, the compositions may be in the form of solutions or suspensions for infusion or for injection, or as lyophilized powders.

"Cosmeceutical" as used herein refers to cosmetic products that have medicinal benefits.

"Differentiation" as used herein refers to the process by which cells become more specialized to perform biological functions. For example, hematopoietic stem cells, hematopoietic progenitors and/or stem cells may change from multipotent stem cells into cells committed to a specific lineage and/or cells having characteristic functions, such as mature somatic cells. Differentiation is a property that is often totally or partially lost by cells that have undergone malignant transformation.

"Enhancement," "enhance" or "enhancing" as used herein refers to an improvement in the performance of or other physiologically beneficial increase in a particular parameter of a cell or organism. At times, enhancement of a phenomenon is quantified as a decrease in the measurements of a specific parameter. For example, migration of stem cells may be measured as a reduction in the number of stem cells circulating in the circulatory system, but this nonetheless may represent an enhancement in the migration of these cells to areas of the body where they may perform or facilitate a beneficial physiologic result, including, but not limited to, differentiating into cells that replace or correct lost or damaged function. In one embodiment, enhancement refers to a 15%, 20%, 30% or greater than 50% reduction in the number of circulating stem cells. In one specific, non-limiting example, enhancement of stem cell migration may result in or be measured by a decrease in a population of the cells of a non-hematopoietic lineage, such as a 15%, 20%, 30%, 50%, 75% or greater decrease in the population of cells or the response of the population of cells. In one embodiment, an enhanced parameter is the trafficking of stem cells. In one embodiment, the enhanced parameter is the release of stem cells from a tissue of origin. In one embodiment, an enhanced parameter is the migration of stem cells. In another embodiment, the parameter is the differentiation of stem cells. In yet another embodiment, the parameter is the homing of stem cells.

"Hematopoietic agent" as used herein refers to a compound, antibody, nucleic acid molecule, protein, cell or other molecule that affects hematopoiesis. A molecular agent can be a naturally-occurring molecule or a synthetic molecule. In some instances, the agent affects the growth, proliferation, maturation, migration or differentiation or release of hematopoietic cells.

"Hematopoietic stem cells" as used in the present invention means multipotent stem cells that are capable of eventually differentiating into all blood cells including, erythrocytes, leukocytes, megakaryocytes, and platelets. This may involve an intermediate stage of differentiation into progenitor cells or blast cells. The term "hematopoietic progenitors", "progenitor cells" or "blast cells" are used interchangeably in the present invention and describe maturing HSCs with reduced differentiation potential, but are still capable of maturing into different cells of a specific lineage, such as myeloid or lymphoid lineage. "Hematopoietic progenitors" include erythroid burst forming units, granulocyte, erythroid, macrophage, megakaryocyte colony forming units, granulocyte, erythroid, macrophage, and granulocyte macrophage colony-forming units.

"Homing" as used herein refers to the process of a cell migrating from the circulatory system into a tissue or organ. In some instances, homing is accomplished via tissue-specific adhesion molecules and adhesion processes. Homing may refer to the migration back to the bone marrow.

"Isolated biological component" (such as a nucleic acid molecule, polypeptide, polysaccharide or other biological molecule) as used herein refers to a biological component that has been substantially separated or purified away from other biological components in which the component naturally occurs. Nucleic acids and proteins may be isolated by standard purification methods, recombinant expression in a host cell, or chemically synthesized.

"Modulation" or "modulates" or "modulating" as used herein refers to upregulation (i.e., activation or stimulation), down regulation (i.e., inhibition or suppression) of a response or the two in combination or apart.

"Migration" as used herein refers to the central process for movement of cells in the development and maintenance of multicellular organisms. Cells often migrate in response to, and towards, specific external signals, commonly referred to as chemotaxis. Migration includes the process of a cell moving from the circulatory system into a tissue or organ. More specifically, circulating stem cells are tethered to the surface of capillary endothelium via expression of adhesion molecules of cell surfaces, resulting in cytoskeletal changes in both endothelium and stem cells, and allowing movement through the capillary wall en route to a tissue and/or organ site. In some instances, homing is accomplished via tissue-specific adhesion molecules and adhesion processes.

"Nutricosmetics" as used herein refers to products and ingredients that act as nutritional supplements to care skin, nails, and hair natural beauty.

"Penetrant" as used herein refers to products and ingredients that increases the permeability of the stratum corneum, allowing large molecules to reach the deeper layers of the dermis.

"Pharmaceutically acceptable carriers" as used herein refer to conventional pharmaceutically acceptable carriers useful in this invention.

"Recruitment" of a stem cell as used herein refers to a process whereby a stem cell in the circulatory system migrates into specific site within a tissue or organ. Recruitment may be facilitated by a compound or molecule, such as a chemoattractant signal or cell receptor. For example, both CXCR4 and SDF-1 have identified roles in stem cell homing and migration.

"Releasing agent" as used herein are mobilization agents capable of promoting the release and egress of stem cells from a tissue of origin. Release of stem cells from a tissue of origin may be demonstrated, for example, by an increase in circulating stem cells in the circulatory or immune system, or by the expression of markers related to egress of stem cells from a tissue of origin, such as bone marrow. For example, a releasing agent increases the number of bone marrow-derived stem cells and/or hematopoietic stem cells in the peripheral blood. In another embodiment, the releasing agent affects the number of stem cells, such as CD34.sup.high (CD34+) cells, circulating in the peripheral blood.

"Stem cells" as used herein are cells that are not terminally differentiated and are therefore able to produce cells of other types. Characteristic of stem cells is the potential to develop into mature cells that have particular shapes and specialized functions, such as heart cells, skin cells, or nerve cells. Stem cells are divided into three types, including totipotent, pluripotent, and multipotent. "Totipotent stem cells" can grow and differentiate into any cell in the body and thus, can form the cells and tissues of an entire organism. "Pluripotent stem cells" are capable of self-renewal and differentiation into more than one cell or tissue type. "Multipotent stem cells" are clonal cells that are capable of self-renewal, as well as differentiation into adult cell or tissue types. Multipotent stem cell differentiation may involve an intermediate stage of differentiation into progenitor cells or blast cells of reduced differentiation potential, but are still capable of maturing into different cells of a specific lineage. The term "stem cells", as used herein, refers to pluripotent stem cells and multipotent stem cells capable of self-renewal and differentiation. "Bone marrow-derived stem cells" are the most primitive stem cells found in the bone marrow which can reconstitute the hematopoietic system, possess endothelial, mesenchymal, and pluripotent capabilities. Stem cells may reside in the bone marrow, either as an adherent stromal cell type, or as a more differentiated cell that expresses CD34, either on the cell surface or in a manner where the cell is negative for cell surface CD34. "Adult stem cells" are a population of stem cells found in adult organisms with some potential for self-renewal and are capable of differentiation into multiple cell types. Other examples of stem cells are marrow stromal cells (MSCs), HSC, multipotent adult progenitor cells (MAPCs), very small embryonic-like stem cells (VSEL), epiblast-like stem cell (ELSC) or blastomere-like stem cell (BLSC).

"Stem cell circulation agent" (SCCA), "mobilization agent", and/or "mobilization factor" as used herein refers to one or more compounds, antibodies, nucleic acid molecules, proteins, polysaccharides, cells, or other molecules, including, but not limited to, neuropeptides and other signaling molecules, that affects the release, circulation, homing and/or migration of stem cells from the circulatory system into tissue or organ. A molecular agent may be a naturally occurring molecule or a synthetic molecule. Examples of mobilization agents include "releasing agents", wherein a releasing agent is capable of promoting the egress of stem cells from a tissue of origin and also "migration agents", wherein a migration agent is capable of promoting the process of a cell moving from the circulatory system into a tissue or organ.

"Subject" as used herein includes all animals, including mammals and other animals, including, but not limited to, companion animals, farm animals and zoo animals. The term "animal" can include any living multi-cellular vertebrate organisms, a category of which non-limiting examples include, a mammal, a bird, a simian, a dog, a cat, a horse, a cow, a rodent, and the like. Likewise, the term "mammal" includes both human and non-human mammals.

"Therapeutically effective amount" as used herein refers to the quantity of a specified composition, or active agent in the composition, sufficient to achieve a desired effect in a subject being treated. For example, this can be the amount effective for enhancing migration of stem cells that replenish, repair, or rejuvenate tissue. In another embodiment, a "therapeutically effective amount" is an amount effective for enhancing trafficking of stem cells, such as increasing release of stem cells, as can be demonstrated by elevated levels of circulating stem cells in the bloodstream. In still another embodiment, the "therapeutically effective amount" is an amount effective for enhancing homing and migration of stem cells from the circulatory system to various tissues or organs, as can be demonstrated be decreased level of circulating stem cells in the bloodstream and/or expression of surface markers related to homing and migration. A therapeutically effective amount may vary depending upon a variety of factors, including but not limited to the physiological condition of the subject (including age, sex, disease type and stage, general physical condition, responsiveness to a given dosage, desired clinical effect) and the route of administration. One skilled in the clinical and pharmacological arts will be able to determine a therapeutically effective amount through routine experimentation.

"Trafficking" as used herein refers to the process of movement of a cell from the tissue of origin, traveling within the circulatory or immune system, and localization towards a site within a tissue and/or organ. Trafficking also includes stem cell mobilization, beginning with release from a tissue of origin, such as egress of stem cells from bone marrow. Trafficking further includes movement of a cell from the tissue of origin, homing by adhesion to the endothelium, transmigration, and final migration within the target tissue and/or organ. Furthermore, trafficking may include the process of movement of a cell of the immune system. One specific, non-limiting example of trafficking is the movement of a stem cell to a target organ, also referred to as migration. Another specific, non-limiting example of trafficking is the movement of a B-cell or a pre-B-cell leaving the bone marrow and moving to a target organ.

"Treat," "treating" and "treatment" as used herein refer to both therapeutic treatment and prophylactic or preventative measures, wherein the object is to prevent or slow down (lessen) the targeted condition, disease or disorder (collectively "ailment") even if the treatment is ultimately unsuccessful. Those in need of treatment may include those already with the ailment as well as those prone to have the ailment or those in whom the ailment is to be prevented.

As described, stem cells are unique cells that possess the capacity to differentiate into more specialized cells. One particular type of stem cell, hematopoietic stem cells (HSCs), are capable of differentiating into many different types of blood cells. In addition, HSCs typically reside in the bone marrow, where proliferation and self-renewal of the cells allows HSCs to be involved in the support and maintenance of the hematopoietic system. Existing scientific literature has chiefly focused on HSCs' potential to develop into hematopoietic lineage cells derivatives. Emerging evidence has further identified the capacity for HSCs to also differentiate into non-hematopoietic, tissue specific cells. Recently, HSCs have been found to possess the capacity to differentiate into a variety of tissue-specific cell types, such as myocytes, hepatocytes, osteocytes, glial cells, and neurons. As a result, aside from forming blood and immune cells, HSCs are responsible for constant maintenance and repair of virtually every tissue and organ of the body.

Similarly, bone marrow stem cells (BMSCs) were recently shown to have significant capability to become cells of other tissues. In the bone marrow, stem cells duplicate using a process known as "asymmetrical cellular division" according to which the two daughter cells are not identical; one cell retains the original DNA and remains in the bone marrow whereas the other cell contains the DNA copies and is released in the blood where it migrates into various tissues in need of repair. BMSCs have been traditionally considered to have little potential for plasticity, being limited in their development to red blood cells, lymphocytes, platelets, bone and connective tissue. However, much scientific work has been published over the past few years that demonstrates the exceptional plasticity of BMSC. For example, after transplantation, BMSCs and HSCs were shown to have the ability to become muscle cells, heart cells, endothelium capillary cells, liver cells, as well as lung, gut, skin, and brain cells. As a further illustrative example, some studies report the ability of HSC to become liver cells upon contact with specific liver-derived molecules, but this process took place within hours. Briefly, HSCs were co-cultured with either normal or damaged liver tissue separated by a semi-permeable membrane (pores large enough to let molecules pass through, but small enough to prevent the passage of cells from one compartment to the other, pore size 0.4 μm). Using immunofluorescence assay methods to detect molecules specific for either HSCs (CD45) or liver cells (albumin), the researchers could follow the transformation of the population of cells placed in the upper compartment. When HSCs were cultured alone for 8 hours, they only expressed CD45 and no albumin, indicating that no HSCs had differentiated into liver cells. However, when HSCs were exposed to injured liver tissue, they rapidly became positive for albumin. Over time, the population of cells positive for CD45 began to decrease as the population positive for albumin began to increase. Albumin-positive cells were seen as early as 8 hours into the procedure and increased in frequency to 3.0% at 48 hours. The conversion was minimal and delayed when HSCs were exposed to undamaged liver (control for injury).

Because HSCs and BMSCs play an important role in the healing and regenerative processes of various tissues and organs in the body beyond their traditional role in maintaining hematopoietic and immune systems of the body, activation and enhancement of stem cell trafficking may amplify these physiological processes and provide a potential therapy for various pathologies. The classic source of HSCs and BMSCs is bone marrow, which includes hip, ribs, sternum and other bone structures. Bone provides a unique regulatory microenvironment for HSCs and BMSCs, which comprises mesenchymal stem cells, including interaction with specific extracellular matrix glycoproteins and a uniquely rich mineral signature. This stem cell "niche" contains a great deal of critical molecular interactions which guide the response of stem cells to specific physiological conditions. The niche may be an important focal point for changes in the state of tissue that result in a change in the regenerative processes rooted in stem cell activity. (Adams and Scadden, 2006)

Beyond populations of stem cells found in bone marrow, stem cells are also present in the peripheral bloodstream of normal, healthy persons. It has been known for decades that a small number of stem and progenitor cells circulate in the bloodstream, but more recent studies have shown that greater numbers of stem cells can be coaxed into mobilization from marrow to blood by injecting the donor with a cytokine, such as granulocyte-colony stimulating factor (G-CSF). Despite this advance, the natural process by which stem cells are released from bone marrow and migrate towards a site within tissue and/or an organ is not fully understood. A leading model involves the chemokine, Stromal-Derived Factor-1 (SDF-1) and its specific receptor, CXCR4. In this capacity, the binding of SDF-1 to CXCR4 leads to adherence of stem cells to bone marrow through increased expression of adhesion molecules on the cell membrane surface. Disruption of adhesion of stem cells to the bone marrow matrix thus promotes mobilization of stem cells into the peripheral bloodstream. (FIG. 1C) Some factors such as G-CSF or IL-8 may interfere with adhesion through elevated activation of proteolytic enzymes or degradation of the SDF-1 ligand. Other types of molecules, such as L-selectin blockers, may instead down-regulate CXCR4 expression which in turn reduces stem cell adhesion to the bone marrow environment. Without wishing to be bound by any theory, enhancing binding of SDF-1 to CXCR4 promote adherence, therefore L-selectin blockers such as sulfated fucans, which reduces CXCR4 expression, can trigger stem cell mobilization.

Stem cells circulating in the peripheral bloodstream are recruited to sites of tissue in need of repair and regeneration through homing and extravasation. This mobilization of stem cells into the bloodstream and subsequent migration to the site of tissue injury results from a combination of mechanical and chemoattractant signals. Mechanical force or other factors may activate L-selectins on the surface of stem cells. Activation of L-selectins, in turn, may promote elevated expression of the receptor, CXCR4. Cells at the site of tissue injury may also secrete SDF-1 ligand, thereby attracting stem cells expressing receptor CXCR4 to the injury site. The interaction of SDF-1 and CXCR4 promotes sufficient adhesion to halt circulation of a stem cell in the peripheral blood stream. (FIG. 1B) Based on this model, L-selectin blockers such as sulfated fucans, may possess a critical capacity to mobilize stem cells into the bloodstream, with subsequent homing, extravasation and migration into tissue promoting regenerative maintenance and repair of cells and tissues in an organism. Whereas G-CSF is released from injured tissue and its presence in the bloodstream triggers stem cell release from bone marrow, dietary supplements composed of L-selectin blockers may possibly support the phenomenon of natural regeneration and repair in the body.

III. Extracts and Compositions of the Embodiments

In some aspects, the present disclosure provides methods and kits comprising a combination of three or four compositions for concomitant use to enhance skin appearance. In some embodiments, the three or four compositions are: a) a microdermabrasion composition, b) transdermal penetrant composition, c) a regenerative composition; and d) a nutricosmetic composition.

Microdermabrasion is a clinical procedure by which abrasive crystals are propelled against the skin under the control of a handheld vacuum system. This procedure abrades the superficial layers of the skin, enhancing skin's permeability and triggering the repair process of the skin. The current disclosure provides for a topical cream or lotion containing specific ingredients that abrase the skin sufficiently to trigger the natural process of skin repair, coupled with the topical application of a regenerative serum or lotion, and the oral intake of a nutricosmetic formula that provides the body with key nutrients to the skin.

In some embodiments, the microdermabrasion composition is a serum, a cream, a lotion, or a paper or a cloth embedded with abrasive agents. In some embodiments, the abrasive agents are solid particles. In some embodiments, the microdermabrasion composition is made using diamond particles. In some embodiments, the microdermabrasion composition in made using crystal particles. In some embodiments, the microdermabrasion composition is made using hematite particles. In some embodiments, the microdermabrasion composition is made using silicon dioxide particles. In some embodiments, the microdermabrasion composition is made using aluminum oxide particles. In some embodiments, the microdermabrasion composition is made using bamboo particles. In some embodiments, the microdermabrasion composition includes one or more microdermabrasion agents selected from the group consisting of: diamond particles, crystal particles, hematite particles, silicon dioxide particles, aluminum oxide particles, and bamboo particles.

In some embodiments, the microdermabrasion composition is made using pearl particles. In some embodiment, the microdermabrasion composition includes one or more of the following components selected from the group including: pearl particles, diamond particles, crystal particles, hematite particles, silicon dioxide particles, aluminum oxide particles, and bamboo particles. In some embodiments, the microdermabrasion composition includes a blend of pearl particles, silicon dioxide particles, and bamboo particles.

In some embodiments, the microdermabrasion composition comprises a carrier. In some embodiments, the carrier is a cream or lotion. In some embodiments, the total concentration of abrasive agents in the carrier lotion or cream is from about 5%, 10%, 15%, 20%, 25%, 30%, 35%, 40%, 45%, to about 50%. In some embodiments, the total concentration of the abrasive agents is about 10%, 20%, 30% or 40%. In some embodiments, the microdermabrasion composition comprises a blend of pearl nacre particles at a concentration of 2-15%, silicon dioxide particles at a concentration of 2-15%, and bamboo particles at a concentration of 2-15%. In some embodiments, the microdermabrasion composition comprises of a blend of pearl nacre particles at a concentration of 8-10%, silicon dioxide particles at a concentration of 3-8%, and bamboo particles at a concentration of 2-6%.

In some embodiments, the transdermal penetrant is a serum, a cream, a lotion or a translucent liquid mixture. In some embodiments the transdermal penetrant composition is made using alkanes. In some embodiments the transdermal penetrant composition is made using laurocapram. In some embodiments the transdermal penetrant composition is made using oil of *Citrus sinensis*. In some embodiments the transdermal penetrant composition is made using oleic acid. In some embodiments the transdermal penetrant composition is made using squalene. In some embodiments the transdermal penetrant composition is made using a mixture of alkanes, laurocapram, oil of *Citrus sinensis*, oleic acid and squalene.

In some embodiments, the transdermal penetrant composition comprises a carrier. In some embodiments, the carrier is a cream or lotion. In some embodiments, the total concentration of penetrating agents is from about 1% to about 25% w/w. In further embodiments, the total concentration of penetrating agents is about 1%, 2%, 3%, 5%, 8%, 10% or 20% w/w. In some embodiments, the penetrating composition comprises a blend of coconut alkanes at a concentration of 1-5%, laurocapram at a concentration of 1-5%, *Citrus sinensis* oil at a concentration of 1-5%, oleic acid at a concentration of 1-5%, and squalene at a concentration of 1-5%. In some embodiments, the penetrating composition comprises a blend of coconut alkanes at a concentration of 3%, laurocapram at a concentration of 3%, *Citrus sinensis* oil at a concentration of 3%, oleic acid at a concentration of 2%, and squalene at a concentration of 1%.

In some embodiments, the regenerative composition is a serum, a cream, or a lotion. In some embodiments, the regenerative composition comprises stem cell-derived cytokines. Non-limiting examples of stem cell-derived cytokines include Human Prolactin or a bio-equivalent, Human Placental Lactogen or a bio-equivalent, Human Epidermal Growth Factor or a bio-equivalent (EGF), Human Fibroblast Growth Factor-1 of a bio-equivalent (FGF-1), Human Stem Cell Factor or a bio-equivalent (SCF), Human Thymosin beta-4 or a bio-equivalent, Human Fibroblast Growth Factor-2 or a bio-equivalent (FGF-2), Human Vasoactive Intestinal Peptide or a bio-equivalent (VIP). In some embodiments, the regenerative composition comprises retinol or retinol derivatives including but not limited to retinoic acid, hydroxypinacolone retinoate, or retinyl retinoate. In some embodiments, the regenerative composition comprises phenylalanine or phenylalanine derivatives, including but not limited to undecylenoyl phenylalanine. In some embodiments, the regenerative composition comprises glucosamine or glucosamine derivatives including but not limited to acetyl glucosamine phosphate, N-acetyl glucosamine-6-phosphate, or N-acetyl-D-glucosamine. In another embodiment the regenerative composition contains MG6P proline lysine copper complex. In another embodiment the regenerative composition contains ferulic acid or ferulic acid derivatives. In some embodiments, the regenerative composition contains *Physalis angulata* or an extract thereof. In some embodiments, the regenerative composition comprises ascorbic acid or an ascorbic acid derivative including but not limited to aminopropyl ascorbyl phosphate, ascorbyl-6-palmitate, 3-O-ethyl ascorbic acid, ascorbyl glucoside or magnesium ascorbyl phosphate. In some embodiments, the regenerative composition comprises hyaluronic acid or a hyaluronic acid derivative including but not limited to hyaluronan, low molecular weight hydrolyzed sodium hyaluronate, or fermented hyaluronic acid.

In some embodiments, the regenerative composition is a serum that contains stem cell-derived cytokines blended with one or more of the following ingredients: hydroxypinacolone retinoate, undecylenoyl phenylalanine, N-acetyl-D-glucosamine, MG6P proline lysine copper complex, *Physalis angulata* or an extract thereof, ferulic acid, aminopropyl ascorbyl phosphate, 3-O-ethyl ascorbic acid, ascorbyl glucoside and low molecular weight hydrolyzed sodium hyaluronate.

In some embodiments, the blend of cytokines and growth factors is a stock solution at a concentration between 5 ppm and 1000 ppm. In some embodiments, the blend of cytokines and growth factors is a stock solution at a concentration between 50 ppm and 500 ppm.

In some embodiments, the blend of cytokines and growth factors is included in the topical product at a concentration between 0.1% and 5%. In some embodiments, the blend of cytokines and growth factors is included in the topical product at a concentration between 0.5% and 3.5%.

In some embodiments, the retinol or retinol derivative is included in the regenerative composition at a concentration between 0.1% and 5%. In some embodiments, the retinol or retinol derivative is included in the regenerative composition at a concentration between 0.5% and 2%. In some embodiments, the retinol derivative is hydroxypinacolone retinoate and is included in the regenerative composition at a concentration between 0.5% and 2%.

In some embodiments, the phenylalanine or phenylalanine derivative is included in the regenerative composition at a concentration between 0.1% and 5%. In some embodiments, the phenylalanine or phenylalanine derivative is included in the regenerative composition at a concentration between 0.5% and 3%. In some embodiments, the phenylalanine derivative is undecylenoyl phenylalanine and is included in the regenerative composition at a concentration between 0.5% and 3%.

In some embodiments, the glucosamine or glucosamine derivative is included in the regenerative composition at a concentration between 0.05% and 5%. In some embodiments, the glucosamine or glucosamine derivative is included in the regenerative composition at a concentration between 0.1% and 2%. In some embodiments, the glucosamine derivative is N-acetyl-D-glucosamine and is included in the regenerative composition at a concentration between 0.1% and 2%.

In some embodiments, the MG6P proline lysine copper complex is included in the regenerative composition at a concentration between 0.05% and 5%. In some embodiments, the MG6P proline lysine copper complex is included in the regenerative composition at a concentration between 0.5% and 2%.

In some embodiments, the ferulic acid or ferulic acid derivate is included in the regenerative composition at a concentration between 0.05% and 5%. In some embodiments, ferulic acid is included in the regenerative composition at a concentration between 0.1% and 1%.

In some embodiments, *Physalis angulata* or an extract thereof is included in the regenerative composition at a concentration between 0.05% and 5%. In some embodiments, *Physalis angulata* or an extract thereof is included in the regenerative composition at a concentration between 0.5% and 2%.

In some embodiments, the ascorbic acid or ascorbic acid derivative is included in the regenerative composition at a concentration between 0.1% and 5%. In some embodiments, the ascorbic acid or ascorbic acid derivative is included in the regenerative composition at a concentration between 1% and 3%. In some embodiments, the regenerative composition comprises a blend of one or more of the following: aminopropyl ascorbyl phosphate, 3-O-ethyl ascorbic acid, magnesium ascorbyl phosphate, and ascorbyl glucoside which are collectively included in the regenerative composition at a concentration between 1% and 5%.

In some embodiments, the hyaluronic acid or hyaluronic acid derivative is included in the regenerative composition at a concentration between 0.1% and 5%. In some embodiments, the hyaluronic acid or hyaluronic acid derivative is included in the regenerative composition at a concentration between 0.5% and 2%. In some embodiments, the hyaluronic acid derivative is low molecular weight hydrolyzed sodium hyaluronate or ultra-low molecular weight hydrolyzed sodium hyaluronate and is included in the topical product at a concentration between 0.5% and 2%.

In some embodiments, the nutricosmetic composition is a powder that can be consumed directly or added to a food such as a bar. In some embodiments, the nutricosmetic composition is a powder that can be mixed with water. In some embodiments, the nutricosmetic composition is a liquid or a drink. In some embodiments, the nutricosmetic composition is a gel.

In some embodiments, the nutricosmetic composition contains ceramides. In some embodiments, the nutricosmetic composition comprises a blend of helicogenic amino acids. Non-limiting examples of helicogenic amino acids include glycine, hydroxyproline, proline, and alanine. In some embodiments, the nutricosmetic composition comprises hyaluronic acid or hyaluronic acid derivatives, including but not limited to hyaluronan and hyaluronic acid. In some embodiments, the nutricosmetic composition comprises N-acetyl-D-glucosamine. In some embodiments, the nutricosmetic composition comprises resveratrol (i.e., trans-resveratrol) isolated from *Vitis vinifera* (red grape), *Fallopia japonica* or *Polygonum cuspidatum* (Japanese knotweed), and/or *Vaccinium corymbosum* (blueberry). In some embodiments, the nutricosmetic composition comprises one or more components selected from the group consisting of: glycine, hydroxyproline, proline, alanine, hyaluronic acid, N-acetyl-D-glucosamine, and trans-resveratrol.

In some embodiments, the nutricosmetic composition provides ceramides at a daily dose of 10 mg to 500 mg. In some embodiments, the nutricosmetic composition provides ceramides at a daily dose of 10 mg to 100 mg.

In some embodiments, the oral product comprises a blend of amino acids providing 0.5 g to 5 g of glycine, 0.25 g to 2.5 g of hydroxyproline, 0.25 g to 2.5 g of proline and 0.1 g to 2 g of alanine. In some embodiments, the nutricosmetic composition provides a blend of amino acids providing 1 g to 2 g of glycine, 0.3 g to 1 g of hydroxyproline, 0.5 g to 1.5 g of proline and 0.1 g to 0.5 g of alanine.

In some embodiments, the nutricosmetic composition provides hyaluronic acid or hyaluronic acid derivatives at a daily dose of 0.1 g to 5 g. In some embodiments, the hyaluronic acid derivative is N-acetyl-D-glucosamine and is provided at a daily dose of 0.2 g to 3 g and/or hyaluronic acid at a daily dose of 150 mg to 1,000 mg.

In some embodiments, the nutricosmetic composition provides resveratrol at a daily dose of 10 mg to 500 mg. In some embodiments, the nutricosmetic composition provides resveratrol at a daily dose of 100 mg to 200 mg.

IV. EXAMPLES

Example 1—Four-Component Skin Care Method

Materials. Hematite is the mineral form of iron (III) oxide ($Fe_2O_3$), it is mined as the main ore of iron. Silicon dioxide can be derived from various forms of sand, such as white sand, black sand, or tan sand. Aluminum oxide occurs in nature as various minerals such as bauxite and corundum. Bamboo particles, pearl particles, diamond particles, crystal particles.

Microdermabrasion enhances collagen formation. FIGS. 1A-1C show the impact of microdermabrasion (MDA) on various skin parameters, using a blend of pearl, silicon dioxide and bamboo particles at a concentration of 25%, with usage 3 times a week for 1 week. FIG. 1A shows MDA increased collagen in the papillary dermis. FIG. 1B shows MDA increased procollagen I in the dermis. FIG. 1C shows procollagen I mRNA in fibroblast isolated from the papillary (■) and reticular (▒) dermis. In summary, MDA 3 times a week for one week triggered an increase in skin collagen that lasted up to 12 weeks. It was accompanied by an increase in procollagen I and procollagen I mRNA in dermal fibroblast.

Figure 2:
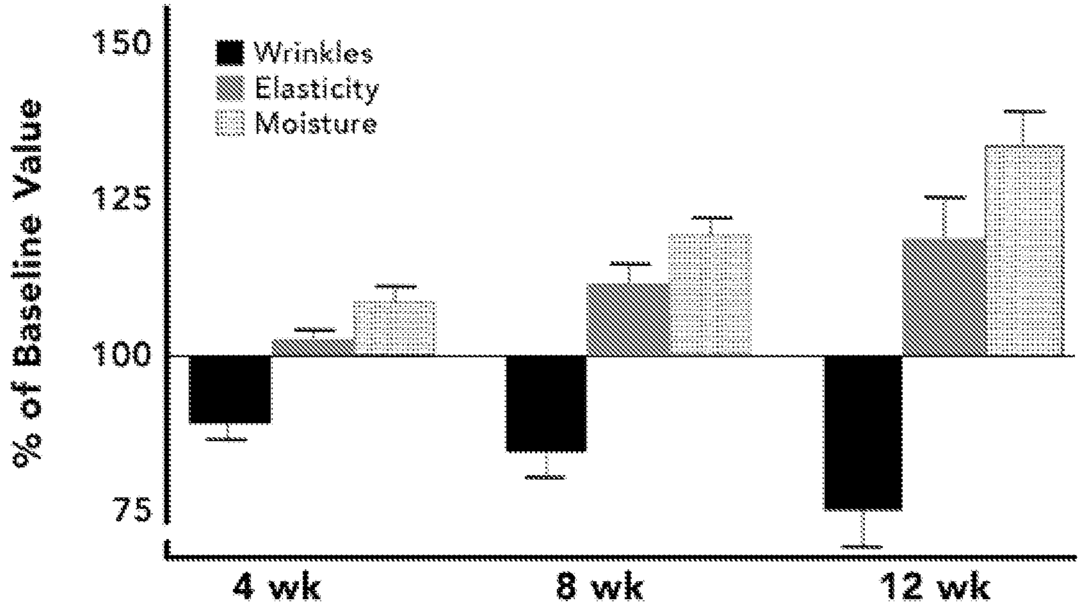
FIG. 2 shows the effect of daily application of a serum containing hydroxypinacolone retinoate, undecylenoyl phenylalanine, N-acetyl-D-glucosamine, MG6P proline lysine copper complex, *physalis angulata* and extract thereof, ferulic acid, aminopropyl ascorbyl phosphate, 3-O-ethyl ascorbic acid, ascorbyl glucoside and low molecular weight hydrolyzed sodium hyaluronate on various skin parameters.

Regenerative composition reduces wrinkles & fine lines. FIG. 2 shows the effect of the daily application of a serum containing hydroxypinacolone retinoate, undecylenoyl phenylalanine, N-acetyl-D-glucosamine, MG6P proline lysine copper complex, *Physalis angulata* or an extract thereof, ferulic acid, aminopropyl ascorbyl phosphate, 3-O-ethyl ascorbic acid and low molecular weight hydrolyzed sodium hyaluronate, on various skin parameters. Daily application of this serum led to 8%, 12% and 25% reductions in wrinkles and fine lines, 5%, 8% and 12% increase in elasticity, and 12%, 22% and 32% increase in moisture retention after 4, 8, and 12 weeks respectively.

Figure 3:
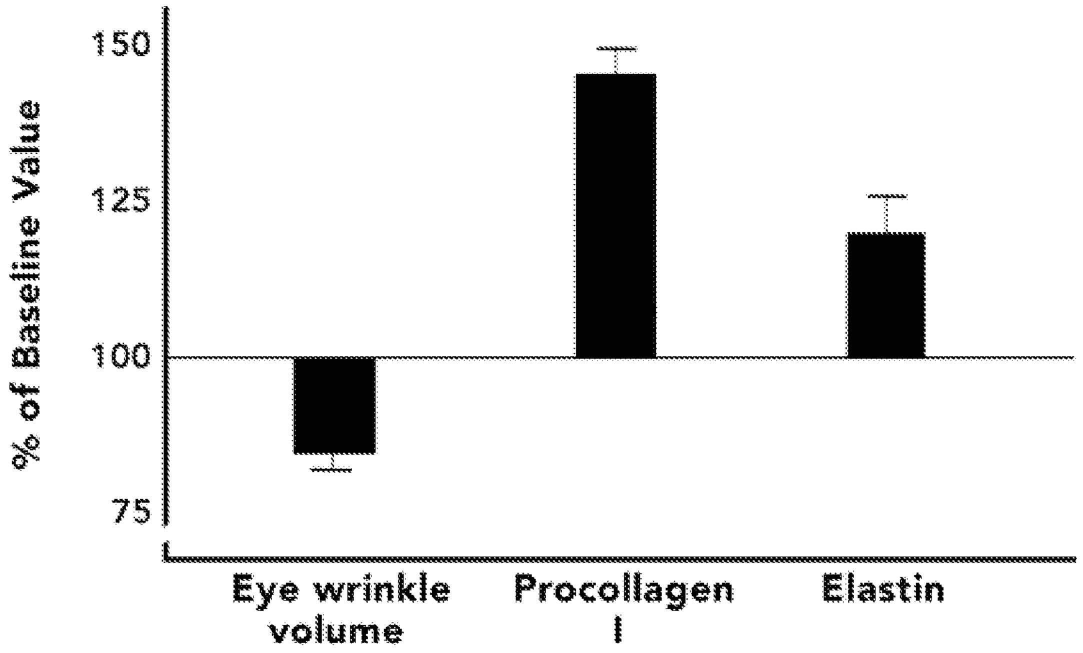
FIG. 3 shows the effect of the consumption of a gel including a blend of amino acids mimicking collagen, namely glycine, hydroxyproline, proline, and alanine, along with hyaluronic acid, N-acetyl-D-glucosamine, and trans-resveratrol on various skin parameters after 8 weeks of daily consumption.

Nutricosmetic composition reduces wrinkles & fine lines. FIG. 3 shows the effect of the consumption of a powder comprising a blend of amino acids mimicking collagen, namely glycine, hydroxyproline, proline, and alanine, along with hyaluronic acid, N-acetyl-D-glucosamine and trans-resveratrol. Daily oral consumption of this nutricosmetic powder led to a 16% reduction in eye wrinkles volume, along with an increase of 51% and 16% in procollagen I and elastin in the skin, respectively.

Figure 4:
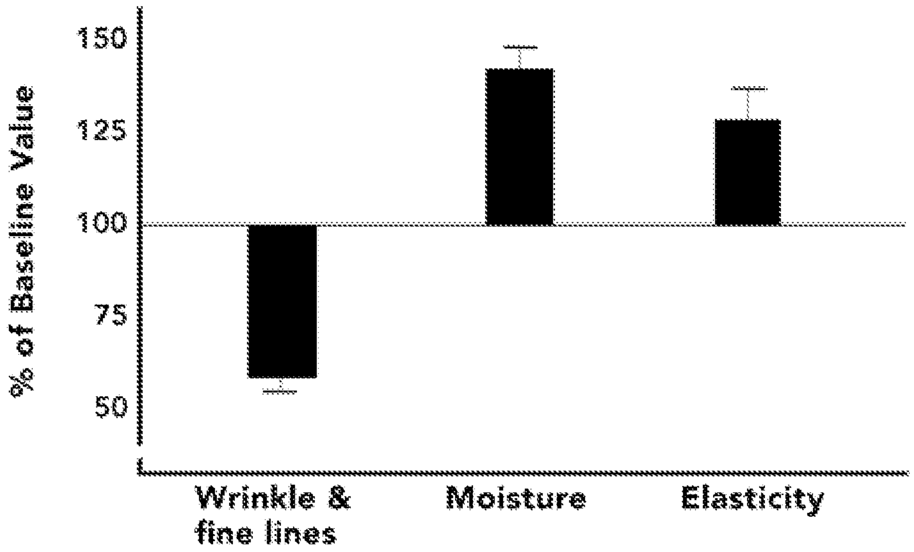
FIG. 4 shows the effect shows the impact of the concomitant use of microdermabrasion, oral nutricosmetic, and topical regenerative serum on various skin parameters after 8 weeks of daily use, as measured using enhanced photography and Skin Imaging Analysis.

Synergy of microdermabrasion, regenerative composition, and nutricosmetic composition reduces wrinkles, fine lines, and skin density. FIG. 4 shows the impact of the concomitant use of microdermabrasion, regenerative cosmeceutical composition, and nutricosmetic composition on various skin parameters, as measured using enhanced photography and Skin Imaging Analysis. Daily use of the program, consisting of daily use of the nutricosmetic composition, daily application of the regenerative serum and bi- or triweekly use of the microdermabrasion composition led to a 41% reduction in wrinkles, along with an increase of 38% and 29% in moisture and elasticity, respectively.

Figure 5:
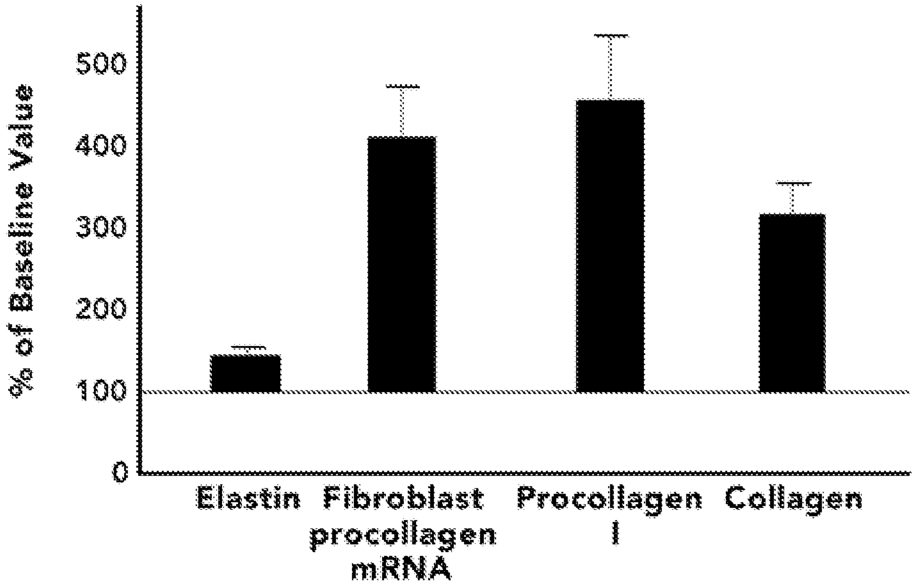
FIG. 5 shows the impact of the concomitant use of microdermabrasion, oral nutricosmetic and topical regenerative serum on various biochemical skin parameters after 8 weeks of daily use.
Figure 6:
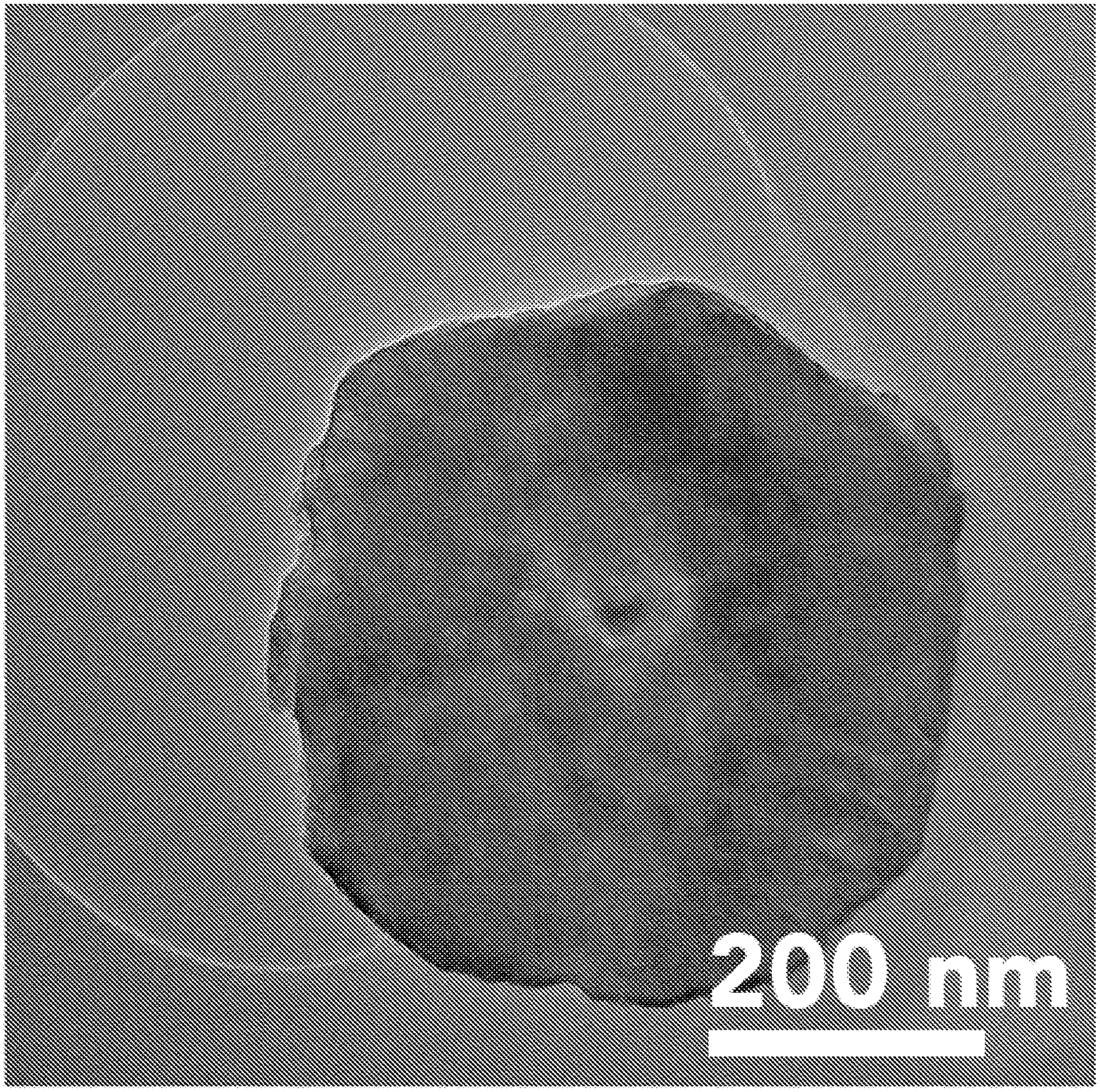
FIG. 6 shows a micrograph of a nacre particle for use as an abrasive agent in microdermabrasion compositions.

Synergy of microdermabrasion, topical product and nutricosmetic Collagen, mRNA. FIG. 5 shows the impact of the concomitant use of microdermabrasion composition, regenerative topical composition, and nutricosmetic composition on various biochemical skin parameters. Daily use of the program, consisting of daily use of the nutricosmetic composition, daily application of the regenerative composition, and bi- or triweekly use of the microdermabrasion composition led to a 50% increase in elastin, a 410% increase in fibroblast procollagen I mRNA, a 450% increase in procollagen I, and a 325% increase in collagen.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Allen et al., "Remington: The Science and Practice of Pharmacy 22$^{nd}$ ed.," *Pharmaceutical Press*, Sep. 15, 2012.

Blanpain C and Fuchs E. Epidermal Stem Cells of the Skin. Annu Rev Cell Dev Biol. 2006; 22: 339-373.

Diegelmann and Evans. Wound healing: An overview of acute, fibrotic and delayed healing. Front Biosci 2004; 9:283-289.

Green et al., "Molecular Cloning: A Laboratory Manual 4th ed.," *Cold Spring Harbor Laboratory Press*, Cold Spring Harbor, N.Y., 2012.

Greenfield, "Antibodies A Laboratory Manual 2$^{nd}$ ed.," *Cold Spring Harbor Press*, Cold Spring Harbor N.Y., 2013.

Hall et al., The comparative role of activator protein 1 and Smad factors in the regulation of Timp-1 and MMP-1 gene expression by transforming growth factor-beta 1, J Biol Chem, 278, 10304 (2003)

Herouy Y. Matrix metalloproteinases in skin pathology (review). Int J Mol Med. 2001; 7(1):3-12.

Hong et al., Immunohistological localization of endogenous unlabeled stem cells in wounded skin. J Histochem Cytochem. 2014 April; 62(4):276-85.

Hornyak et al., "Introduction to Nanoscience and Nanotechnology," CRC Press, 2008.

Hunt T K. The physiology of wound healing. Ann Emergency Med 1988; 17:1265-1273.

Matrisian L M, The matrix-degrading metalloproteinases. Bioessays. 1992; 14(7):455-463.

Maxson et al., Concise Review: Role of Mesenchymal Stem Cells in Wound Repair. Stem Cells Translational Medicine 2012; 1:142-149

Paladini et al., Onset of re-epithelialization after skin injury correlates with a reorganization of keratin filaments in wound edge keratinocytes: defining a potential role for keratin 16. J Cell Biol. 1996; 132(3):381-397.

Parks W C. Matrix metalloproteinases in repair. Wound Repair Regen. 1999; 7(6):423-432

Singleton et al., "Dictionary of Microbiology and Molecular Biology 3$^{rd}$ ed.," revised ed., *J Wiley & Sons,* 2006.

Smith, "March's Advanced Organic Chemistry Reactions, Mechanisms and Structure 7$^{th}$ ed.," *J Wiley & Sons Wiley-Blackwell*, Nov. 28, 2012.

Tonnesen et al., Angiogenesis in wound healing. J Invest Dermatol Symp Proc 2000; 5:40-46.

Velnar et al., The wound healing process: An overview of the cellular and molecular mechanisms. J Int Med Res 2009; 37:1528-1542. Wang and Chang. Induction of disease-associated keratin 16 gene expression by epidermal growth factor is regulated through cooperation of transcription factors Sp1 and c-Jun. J Biol Chem. 2003; 278(4445848-45857.

Wang et al., Activation of extracellular signal—regulated kinase signaling by epidermal growth factor mediates activation and p300 recruitment in keratin 16 gene expression. Mol Pharmacol. 2006; 69(1):85-98.

What is claimed is:

1. A method of conditioning the skin of a subject in need thereof, comprising:

a) abrading a skin surface of a subject by applying a microdermabrasion composition comprising solid pearl particles to the skin surface of the subject to trigger tissue repair at the abraded skin surface;

b) applying a topical regenerative cosmeceutical composition comprising hydroxypinacolone retinoate, undecylenoyl phenylalanine, N-acetyl-D-glucosamine, MG6P (methylglucoside-6-phosphate) proline lysine copper complex, *Physalis angulata* or an extract thereof, ferulic acid, aminopropyl ascorbyl phosphate, 3-O-ethyl ascorbic acid, ascorbyl glucoside, and hydrolyzed sodium hyaluronate to the abraded skin surface of step (a); and c) administering an oral nutricosmetic composition comprising glycine, hydroxyproline, proline, alanine, hyaluronic acid, N-acetyl-D-glucosamine, and resveratrol to the subject.

2. The method of claim 1, wherein the microdermabrasion composition comprises an additional abrasive agent selected from the group consisting of diamond, hematite, silicon dioxide, aluminum oxide, and bamboo particles.

3. The method of claim 1, wherein the total concentration of the solid pearl particles in the microdermabrasion composition is from about 5% to about 50% w/w.

4. The method of claim 1, wherein the microdermabrasion composition comprises pearl, silicon dioxide, and bamboo particles.

5. The method of claim 4, wherein the total concentration of the pearl particles in the microdermabrasion composition is from about 2% to about 15% w/w.

6. The method of claim 1, wherein the topical regenerative composition further comprises a stem cell-derived cytokine.

7. The method of claim 6, wherein the stem-cell derived cytokine is Human Prolactin or a bio-equivalent, Human Placental Lactogen or a bio-equivalent, Human Epidermal Growth Factor or a bio-equivalent (EGF), Human Fibroblast Growth Factor-1 of a bio-equivalent (FGF-1), Human Stem Cell Factor or a bio-equivalent (SCF), Human Thymosin beta-4 or a bio-equivalent, Human Fibroblast Growth Factor-2 or a bio-equivalent (FGF-2), Human Vasoactive Intestinal Peptide or a bio-equivalent (VIP).

8. The method of claim 6, wherein the concentration of the stem cell-derived cytokine is from about 0.05% to about 5%.

9. The method according to claim 1, wherein the nutricosmetic composition is formulated as a unit dose.

10. The method of claim 1, wherein the total daily dose administered of each of the components of the oral nutricosmetic composition is independently from about 0.01 g to 5 g.

11. The method of claim 1, wherein the method enhances the appearance of the skin, skin tone, skin moisture or hydration, skin elasticity, or collagen formation.

12. A cosmetic kit comprising:

a) a topical microdermabrasion composition comprising solid pearl particles;

b) a topical regenerative cosmeceutical composition comprising hydroxypinacolone retinoate, undecylenoyl phenylalanine, N-acetyl-D-glucosamine, MG6P proline lysine copper complex, *Physalis angulata* or an extract thereof, ferulic acid, aminopropyl ascorbyl phosphate, 3-O-ethyl ascorbic acid, ascorbyl glucoside, and hydrolyzed sodium hyaluronate; and c) a nutricosmetic composition comprising glycine, hydroxyproline, proline, alanine, hyaluronic acid, N-acetyl-D-glucosamine, and resveratrol.

13. The method of claim 1, wherein the pearl particles are pearl nacre particles.

* * * * *